(12) United States Patent
Mayorga et al.

(10) Patent No.: US 8,173,213 B2
(45) Date of Patent: May 8, 2012

(54) PROCESS STABILITY OF NBDE USING SUBSTITUTED PHENOL STABILIZERS

(75) Inventors: Steven Gerard Mayorga, Oceanside, CA (US); Mary Kathryn Haas, Emmaus, PA (US); Mark Leonard O'Neill, Allentown, PA (US); Dino Sinatore, Whitehall, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 433 days.

(21) Appl. No.: 12/470,002

(22) Filed: May 21, 2009

(65) Prior Publication Data

US 2009/0297711 A1  Dec. 3, 2009

Related U.S. Application Data

(60) Provisional application No. 61/056,734, filed on May 28, 2008.

(51) Int. Cl.
- *C09K 15/08* (2006.01)
- *C10L 1/183* (2006.01)
- *C23C 16/40* (2006.01)
- *H01L 21/00* (2006.01)

(52) U.S. Cl. ......... 427/255.37; 427/255.18; 427/255.23; 427/255.28; 252/182.29; 252/404; 438/758

(58) Field of Classification Search ............. 427/250, 427/255.18, 255.19, 255.23, 255.29, 255.31, 427/255.37, 255.4, 255.28; 585/6; 252/182.29; 252/404; 438/758, 778
See application file for complete search history.

(56) References Cited

U.S. PATENT DOCUMENTS

| | | | |
|---|---|---|---|
| 3,409,683 A * | 11/1968 | Britton | 585/3 |
| 4,094,916 A * | 6/1978 | Thomas | 585/255 |
| 4,979,545 A | 12/1990 | Fair | |
| 5,279,338 A | 1/1994 | Goossens | |
| 5,372,754 A | 12/1994 | Ono | |
| 5,451,260 A | 9/1995 | Versteeg et al. | |
| 5,536,323 A | 7/1996 | Kirlin et al. | |
| 5,551,309 A | 9/1996 | Goossens et al. | |
| 5,607,002 A | 3/1997 | Siegele et al. | |
| 5,835,678 A | 11/1998 | Li et al. | |
| 5,882,416 A | 3/1999 | Van Buskirk et al. | |
| 5,992,830 A | 11/1999 | Daubs et al. | |
| 6,159,871 A | 12/2000 | Loboda et al. | |
| 6,217,658 B1 | 4/2001 | Orczyk et al. | |
| 6,383,555 B1 | 5/2002 | Hayashi et al. | |
| 6,479,110 B2 | 11/2002 | Grill et al. | |
| 6,541,398 B2 | 4/2003 | Grill et al. | |
| 6,583,048 B1 | 6/2003 | Vincent et al. | |
| 6,596,627 B2 | 7/2003 | Mandal | |
| 6,604,492 B2 | 8/2003 | Porter et al. | |
| 6,633,076 B2 | 10/2003 | Krishnaraj et al. | |
| 6,756,323 B2 | 6/2004 | Grill et al. | |
| 6,815,373 B2 | 11/2004 | Singh et al. | |
| 6,846,515 B2 | 1/2005 | Vrtis et al. | |
| 6,914,335 B2 | 7/2005 | Andideh et al. | |
| 2003/0186035 A1 * | 10/2003 | Cruce et al. | 428/292.4 |
| 2004/0127070 A1 | 7/2004 | Teff et al. | |
| 2007/0057234 A1 * | 3/2007 | Teff et al. | 252/397 |
| 2007/0057235 A1 | 3/2007 | Teff et al. | |

FOREIGN PATENT DOCUMENTS

| | | |
|---|---|---|
| JP | 2001-139500 A | 5/2001 |
| WO | 2007/033075 A2 | 3/2007 |
| WO | 2007/033123 A2 | 3/2007 |

OTHER PUBLICATIONS

Butylated hydroxytoluene, Online chemical journal "LOOKCHEM" [online] no date [retrieved on Sep. 21, 2011], Retrieved from the Internet: <URL: www.lookchem.com/cas-128/128-37-0.html>.*

* cited by examiner

*Primary Examiner* — Matthew Daniels
*Assistant Examiner* — Dennis Cordray
(74) *Attorney, Agent, or Firm* — Joseph D. Rossi

(57) ABSTRACT

A stabilized cyclic alkene composition comprising one or more cyclic alkenes, and at least one stabilizer compound having the Formula (I), $$R^1,R^2,R^3,R^4,R^5(C_6)OH \qquad \text{Formula (I)}$$

wherein R' through $R^5$ can each independently be H, OH, $C_1$-$C_8$ linear, branched, or cyclic alkyl, $C_1$-$C_8$ linear, branched, or cyclic alkoxy or substituted or unsubstituted aryl, and wherein the stabilizer compound is present in an amount greater than 200 ppm up to 20,000 ppm and has a boiling point lower than 265° C.
A method for forming a layer of carbon-doped silicon oxide on a substrate, which uses the stabilized alkene composition and a silicon containing compound.

4 Claims, 4 Drawing Sheets

Figure 1.
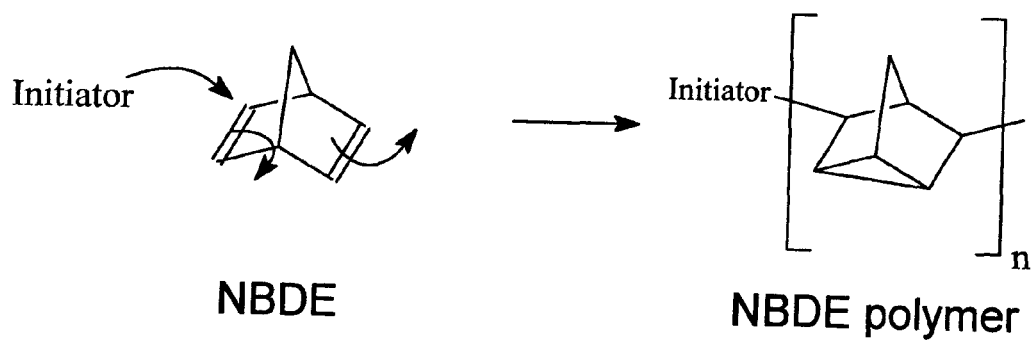
NBDE → NBDE polymer
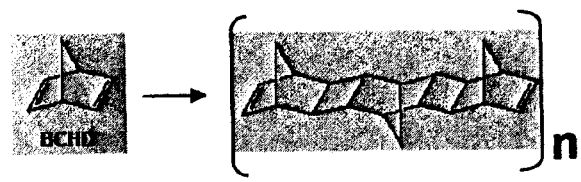
Figure 2

PROCESS STABILITY OF NBDE USING SUBSTITUTED PHENOL STABILIZERS

CROSS REFERENCE TO RELATED APPLICATIONS

This patent application claims the benefit of U.S. Provisional Patent Application Ser. No. 61/056,734 filed May 28, 2008.

BACKGROUND OF THE INVENTION

The present disclosure is directed to cyclic alkene derivatives stabilized with one or more stabilizer compounds to reduce or eliminate residue formation upon evaporation of such compositions, and methods for use of such compositions to form dielectric films.

The semiconductor industry requires numerous types of thin and thick films to prepare semiconductor devices, many of which are based on silicon. The elemental composition of these films is typically some combination of silicon and carbon with various combinations of oxygen, hydrogen, and fluorine. Relevant patents are: U.S. Pat. No. 6,914,335, Andideh et al. and U.S. Pat. No. 6,846,515, Vrtis et al. A frequently used process is chemical vapor deposition (CVD), and there are numerous variations of this process.

In a typical chemical vapor deposition process, a silicon containing compound is introduced into a deposition chamber containing a substrate to be coated. The silicon containing compound is then chemically or physically altered (i.e., reacted with another component, or subjected to application of an energy source such as radiation, heat (thermal CVD), or plasma (PECVD), etc.) to deposit a film on the substrate. Deposited films containing only silicon and oxygen (i.e., silicon oxide) have a dielectric constant of approximately 4 in the absence of pores, while films that also contain carbon (i.e., carbon doped silicon oxide) and/or pores often have dielectric constants lower than 4. Films with a dielectric constant below about 2.7 are preferred for newer semiconductor devices. A relevant patent is: U.S. Pat. No. 6,583,048, Vincent et al.

The properties of a layer deposited on a substrate, such as dielectric constant, film hardness and refractive index, are influenced by changing the composition of the chemistry that is fed into the film deposition tool and the process employed. The film properties can be tuned by changing the identity of the silicon containing compound by using a different flow gas, by using one or more different reactive gases, or by using post-deposition anneal techniques. Another means to affect the layer properties is to use a combination of silicon containing compounds or to combine a silicon containing compound(s) with one or more additive compounds. These techniques can be employed to alter the chemical composition of the film to adjust the film to the desired properties. Relevant patents are: U.S. Pat Nos. 6,633,076, 6,2176,58, 6,159,871, 6,479,110 and 6,756,323.

An alternative method of use for the additive compound is to employ compounds whose fragments or atoms are only temporarily resident in the film. The film can be post-treated to drive the fragments or atoms out of the film using radiation or a combination of radiation and reactive gases, such as oxygen, to create voids in the resulting film. This approach affects the properties (e.g. dielectric constant) of the deposited film. The compounds employed in this manner are described as porogens.

Typical porogens used in this type of approach are predominately composed of carbon and hydrogen. Relevant patents are: U.S. Pat. Nos. 6,846,515 and 6,756,323.

High volume semiconductor manufacturing places stringent demands on the equipment and on the purity and stability of the chemistries that flow through the equipment. Even trace amounts of some contaminants can degrade the properties of a deposited film. A chemical that is sent through chemical lines and a vaporizer means is expected to transport and vaporize cleanly and leave behind little or no residue during extended use. The longer a piece of equipment can operate between scheduled or unscheduled maintenance periods (such as, to clean out chemical lines or a vaporizer means that is fouled or clogged with polymeric residue), the more productive the tool is, making it more cost-effective. A deposition tool that must be shut down often for cleaning and maintenance is not as appealing to semiconductor manufacturing customers. Thus, continuous, long term operation of equipment is desirable. Vaporizer means can include several types of vaporization apparatuses, including, but not limited to, heated vaporizers (see U.S. Pat. Nos. 6,604,492, 5,882,416, 5,835,678, and references therein), bubbler ampoules (see U.S. Pat. Nos. 4,979,545, 5,279,338, 5,551,309, 5,607,002, 5,992,830 and references therein), flash evaporators (see U.S. Pat. No. 5,536,323 and references therein) and misting apparatuses (see U.S. Pat. Nos. 5,451,260, 5,372,754, 6,383,555, and references therein).

These purity and stability requirements are often difficult to achieve. Many materials may oxidize, polymerize or rearrange to some degree. Even small amounts of such byproducts may be undesirable for many semiconductor applications.

1,3,5,7-Tetramethylcyclotetrasiloxane (TMCTS) is a representative silicon containing compound which can be employed to produce low k dielectric films and is an example of the difficulty in maintaining stability. Initial work to establish reliable manufacturing processes was hampered by the product gelling at different points in the deposition process, including the chemical lines, vapor delivery lines, and within the deposition chamber. This indicated that the stability of pure TMCTS was not sufficient, and a variety of additives were studied. It was found that stabilizers were highly effective to stabilize TMCTS against exposure to air, specifically oxygen, for extended periods of time at ambient or elevated temperatures. When stabilizer-stabilized TMCTS is used now in semiconductor manufacturing, processes are more stable, and gel formation in a deposition tool is reduced significantly. A relevant patent is Teff et al. U.S. Patent Application Publication No. 2004/0127070.

BRIEF SUMMARY OF THE INVENTION

The present disclosure provides a stabilized cyclic alkene composition comprising:

a) one or more substituted or unsubstituted cyclic alkenes, and b) a stabilizer composition comprising at least one compound of Formula (I), wherein the stabilizer composition is present in a concentration greater than 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl with the proviso that the components of the stabilizer composition have boiling point(s) lower than 265° C.

c) Formula (I):

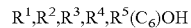

$R^1, R^2, R^3, R^4, R^5(C_6)OH$

The present disclosure further provides a process using a cyclic alkene composition for forming a layer of carbon-doped silicon oxide on a wafer. The process comprises the steps of:

a) providing a cyclic alkene composition in a container, a silicon containing compound in a container, a film deposition tool, a film deposition chamber within said film deposition tool, a means for connecting the containers to the film deposition chamber within said film deposition tool, a stream of carrier gas to sweep the cyclic alkene composition and the silicon containing compound through the connecting means into the film deposition chamber, and a substrate within the film deposition chamber of the film deposition tool;

b) introducing the vapors of the cyclic alkene composition and the silicon containing compound into the carrier gas stream;

c) transporting the vapor of the cyclic alkene composition and silicon containing compound into the film deposition chamber; and d) using one or more energy means, to form a carbon doped silicon oxide film on the substrate, wherein said cyclic alkene composition comprises:

1) one or more substituted or unsubstituted cyclic alkenes, and 2) a stabilizer composition comprising at least one compound of Formula (I), wherein the stabilizer composition is present in a concentration greater than 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl with the proviso that the components of the stabilizer composition have boiling point(s) lower than 265° C.

3) Formula (I):

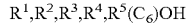

$$R^1,R^2,R^3,R^4,R^5(C_6)OH$$

BRIEF DESCRIPTION OF SEVERAL VIEWS OF THE DRAWINGS

FIG. 1 is a schematic illustration of the mechanism of static, room temperature degradation of 2,5-Norbornadiene (NBDE) rendering an oligomer of "n" length as an approximation of one theory of degradation/oligomerization, which shall not be limiting but is the inventors theory, resulting in non-volatile, soluble residues.

FIG. 2 is a schematic illustration of the mechanism of dynamic, elevated temperature degradation of 2,5-Norbornadiene, also known by the acronym "BCHD", at the injector of a liquid delivery vaporization device for a reaction chamber where the composition is utilized, showing a theoretical mechanism of oligomerization resulting in non-volatile residues, which are industrially unacceptable.

DETAILED DESCRIPTION OF THE INVENTION

Figure 3:
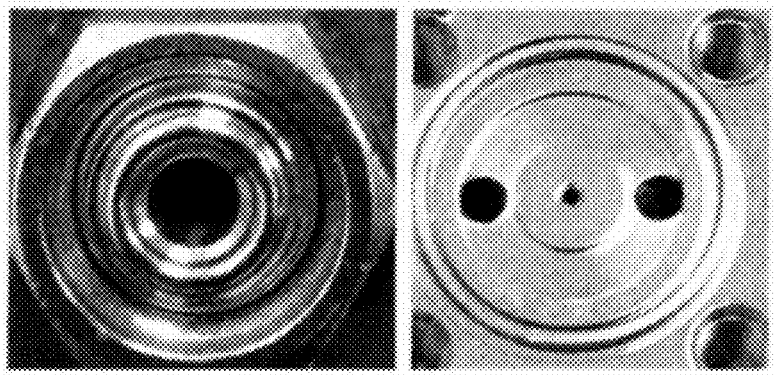
FIG. 3 are photographs of an injector port on the left and an injector face plate on the right prior to contact with NBDE showing the absence of any residue.

The semiconductor industry requires numerous types of thin and thick films to prepare semiconductor devices. A frequently used process to prepare these films is chemical vapor deposition and there are numerous variations of this process. In a typical chemical vapor deposition process, a silicon containing compound is introduced into a deposition chamber containing the substrate to be coated. The silicon containing compound is then chemically or physically altered (reacted with another component, or subjected to application of an energy source such as radiation, heat (thermal CVD), or plasma (PECVD), etc.) to deposit the film on the substrate.

High volume semiconductor manufacturing places stringent demands on the film deposition equipment and on the purity and stability of the chemistries that flow through the equipment. Even trace amounts of some contaminants can degrade the properties of a deposited film. A chemical that is sent through chemical lines and a vaporizer means is expected to transport and vaporize cleanly and leave behind little or no residue during extended use. The longer a piece of equipment can operate between scheduled or unscheduled maintenance periods (such as, to clean out chemical lines or a vaporizer means that is fouled or clogged with polymeric residue), the more productive the tool is, making it more cost-effective. A deposition tool that must be shut down often for cleaning and maintenance is not as appealing to semiconductor manufacturing customers. Thus, continuous, long term operation of equipment is desirable.

These purity and stability requirements are often difficult to achieve. Many materials may oxidize, polymerize or rearrange to some degree. Even small amounts of such byproducts may be undesirable for many semiconductor applications. Thus materials used in the semiconductor industry may require additives to prevent formation of undesired side reactions before reaching a deposition chamber.

Cyclic alkenes are materials of interest for chemical vapor deposition to form low k dielectric films in the semiconductor industry that require additives to be stabilized.

Chemicals, including additives, that are useful for the semiconductor industry are typically limited to species that have a boiling point lower than 300° C. to ensure that they are sufficiently volatile to avoid accumulation at the injector.

Preferably, NBDE is selected as the precursors for the production of low k dielectric materials.

NBDE (2,5-Norbornadiene) is a particularly attractive precursor candidate because of its high degree of chemical unsaturation which is believed to give rise to favorable deposition properties such as high deposition rates and high utilization efficiencies. The utilization efficiency pertains to the amount of hydrocarbon porogen precursor required relative to the organosilicate precursor in order to deposit a porous low k film of a given dielectric constant. Unfortunately, the high degree of unsaturation of NBDE may also be responsible for its intrinsic thermal instability with respect to oligomerization.

Laboratory evaluation has shown that NBDE degrades at ambient temperature to form soluble oligomeric species. The degradation products have been shown by solids-probe mass spectrometry to contain NBDE oligomers, such as dimers, trimers, tetramers, pentamers, hexamers, etc. Additional GPC (gel permeation chromatography) analysis of the isolated residue resulting from degradation reveals the presence of oligomers with an average molecular weight of >3200 and possibly as high as 100,000 or more, corresponding to hundreds or thousands of molecular units of NBDE.

The degradation of NBDE raises a number of issues for its application as a precursor for making low k films. The high rate of degradation suggests that the chemical composition and physical properties of the precursor will change overtime. These changes are very likely to negatively influence the commercial viability of the NBDE by adversely impacting the storage shelf-life, precursor processability, and the ability of end-users to produce a consistent quality film that conforms to the rigorous production standards and specifications of thin film manufacturers. These factors are individually discussed in further detail below.

In order for precursor materials to be viable in a manufacturing environment they need to satisfy practical requirements with respect to product shelf-life. The product shelf life provides the end user or manufacturer assurance that the subject chemical will meet certain minimal standards of performance if used within the time allotted by the shelf-life specification. In practice the product shelf life is often defined by the length of time a chemical will meet pre-determined purity requirements with respect to key chemical components. The degradation rate of NBDE or other unsaturated hydrocarbons must be reduced to an acceptable level to ensure that it conforms to minimal shelf-life requirements, and as such, will be viable in a manufacturing environment as precursors for the production of low k films.

A second problem posed by the degradation of NBDE or other unsaturated hydrocarbon is related to the chemical delivery method commonly used for such liquid precursors. Volatile liquids such as NBDE or other unsaturated hydrocarbons are commonly delivered by a technique referred to in the industry as DLI, or direct liquid injection. For DLI systems the precursor is delivered to the tool as a liquid at a precisely metered rate through an injector port into the heated injection manifold. The manifold is operated at elevated temperature and reduced pressure to cause the precursor to rapidly vaporize, prior to transport of the vapor to the deposition chamber. As illustrated in the present disclosure, such demanding conditions encountered during the chemical delivery process itself, may be sufficient to cause freshly distilled NBDE (i.e., no significant oligomeric content) to instantaneous degrade at the injector, thus producing a significant concentration of non-volatile oligomers resulting in flow problems or plugging. Alternatively, the delivery of a partially degraded chemical, such as unstabilized, aged NBDE, that is expected to contain a significant concentration of dissolved non-volatile oligomeric decomposition products, is similarly expected to cause flow problems or plugging at the injector. The DLI delivery method will indiscriminately transfer the NBDE or unsaturated hydrocarbon liquid along with any dissolved oligomeric degradation products to the tool. The oligomers are expected to be either less volatile or non-volatile under the temperature and pressure conditions experienced at the injector. The delivery of low volatility oligomeric components would result in the gradual accumulation of said species in the tool plumbing which is expected to have a detrimental impact on tool operation and/or film quality.

Another possible negative consequence of using degraded NBDE is related to possible on-tool precipitation issues that may result from contact of partially degraded NBDE with another chemical such as DEMS (diethoxymethylsilane). Instantaneous precipitation of the oligomers is expected to occur if NBDE containing an appreciable concentration of dissolved oligomeric degradation products comes into contact with DEMS, or another liquid of higher polarity than NBDE itself. The precipitation is caused by an increase in the overall polarity of the liquid blend that occurs when a substantial quantity of DEMS is added to aged, unstabilized NBDE. On-tool precipitation is expected to occur in the event that NBDE, containing oligomeric degradation products, comes into contact with a more polar component, such as DEMS, during the co-deposition of porogen and silica source materials. Such on-tool precipitation would cause increased tool down-time and/or necessitate more frequent tool preventative maintenance in order to avoid precursor plugging or flow problems. Oligomer precipitation may also cause indirect problems by adversely impacting film quality, and/or increasing on-wafer particle count, etc.

Our laboratory tests have shown that NBDE degrades at a rate of ~1.4 wt. % per year at ambient temperature, which corresponds to 1.6 ppm per hour. At 80° C. the rate of degradation increases 160-fold to 258 ppm/hr. Butylated hydroxytoluene is often used to reduce the degradation of NBDE, however 200 ppm of BHT will reduce its rate of degradation by only 31%, such that it degrades at 179 ppm/hr at 80° C. Therefore, although BHT does slow down the degradation rate of NBDE, it does not slow it down enough to make it practical for use in the current application.

Our laboratory testing of the stabilizers MHQ and 4MP covered at concentration of less than 200 ppm in US Patent Application by Teff et al. (US20070057235,) showed that they were indeed more effective than BHT for inhibiting polymerization of NBDE under accelerated ageing conditions intended to simulate prolonged storage under static conditions. For example, 200 ppm of MHQ decreased the degradation rate of NBDE to 53 ppm per hour at 80° C.; 200 ppm of 4MP was slightly more effective, dropping the degradation rate to 47 ppm per hour at 80° C. These represent 79% and 82% reduction, respectively, in the rate of degradation relative to the unstabilized NBDE. Thus, MHQ and 4MP were confirmed to be more effective than BHT for stabilizing NBDE. The same level of the latter inhibitor only decreased the NBDE degradation rate by 31% under comparable static test conditions. Therefore, although MHQ and 4MP were more effective than BHT, they also have limited ability to suppress the oligomerization of NBDE, assuming a maximum concentration of 200 ppm as disclosed in the aforementioned application by Teff et al.

In the present invention, NBDE or other unsaturated hydrocarbons can be stabilized by the addition of an appropriate amount of phenolic stabilizer or substituent phenols represented by the general formula:

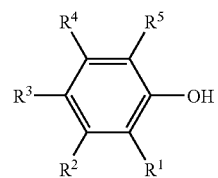

Wherein $R^1$ through $R^5$ can each independently be H, OH, $C_1$-$C_{18}$ linear, branched, or cyclic alkyl, $C_1$-$C_{18}$ linear, branched, or cyclic alkoxy or substituted or unsubstituted aryl, and wherein the substituted phenol is present in the concentration range of 200 ppm to 20,000 ppm.

An effective stabilizer must address both long term storage stability and process stability under chemical delivery conditions. Evaluation of substituted phenols of the general formula $C_6R_5$—OH, such as 4-methoxyphenol has established that higher levels of this stabilizer, such as 1000 ppm, are necessary to impart stability to NBDE under dynamic process conditions. The lower level of stabilizer claimed by Teff et al., less than 200 ppm, is sufficient to impart some degree of stability for storage purposes, but is not adequate to provide the necessary stabilization under more demanding process conditions in which NBDE is subjected to rapid pressure drop, high gaseous flow rates, and high velocity impingement onto various metallic surfaces during the vaporization process. The purpose of the present application is to disclose the use of higher concentrations of substituted phenol stabilizers of the general formula, $C_6R_5$—OH, in order to produce a stabilized NBDE which possesses both storage and process stability.

The compositions of the present disclosure exhibit enhanced dynamic stability. In addition to static results, our laboratory testing shows that NBDE monomer degrades at a rate of greater than 0.5% by weight during DLI through an injector at 85 C. 200 ppm of 4MP as disclosed in US Patent Application 20070057235 by Teff et al. is insufficient for dynamic stability at an injector temperature of 85 C during delivery of the precursor through a heated vaporizer and vapor line.

In one embodiment of the present disclosure, the cyclic alkene composition comprises:
a) one or more substituted or unsubstituted cyclic alkenes, and
b) an stabilizer compound, wherein the stabilizer compound is a phenolic compound having a boiling point lower than 265° C. and is present in a concentration greater than 200 ppm and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl, having the formula:

$$R^1,R^2,R^3,R^4,R^5(C_6)OH$$

A cyclic alkene is hereby defined as any carbocyclic compound having a nonaromatic double bond in a nonaromatic ring. Examples of classes of cyclic alkene include, but are not limited to cycloalkenes, cycloalkadienes, cycloalkatrienes, cycloalkatetraenes, aromatic-containing cycloolefins, polycyclic alkenes, polycyclic alkadienes, polycyclic alkatrienes, polycyclic alkatetraenes, and mixtures thereof.

A preferred class of cyclic alkenes are singly or multiply unsaturated cyclic alkenes of the general formula CnH2n–c–yRy where n is the number of carbons in the primary cyclic structure, x is the number of unsaturated sites in the primary cyclic structure, and y is the number of non hydrogen substituents, R, on the primary cyclic structure. In this class of cyclic alkenes, n is an integer from 4 to 18, x is an integer and $1 \leq x \leq n/2$, y is an integer and $0 \leq y \leq 2n-2x$, and each R can independently be C1-C18 linear, branched, unsaturated, or cyclic alkyl, $C_1$-$C_{18}$ linear, branched, unsaturated, or cyclic alkoxy, substituted or unsubstituted aryl, or a substituted silicon containing substituent. A more preferred range of values for n is 6 to 14, and a most preferred range is 8 to 12. Examples of this class include, but are not limited to, t-butylcyclohexene, alpha-terpinene, limonene, gamma-terpinene, 1,5-dimethyl-1,5-cyclooctadiene, vinylcyclohexene, cyclobutene, methylcyclobutene, dimethylcyclobutene, trimethylcyclobutene, ethylcyclobutene, diethylcyclobutene, triethylcyclobutene, methoxycyclobutene, methylmethoxycyclobutene, cyclohexylcyclobutene, isopropylcyclobutene, isopropenylcyclobutene, cyclopentene, methylcyclopentene, dimethylcyclopentene, trimethylcyclopentene, methoxycyclopentene, methylmethoxycyclopentene, cyclohexylcyclopentene, isopropylcyclopentene, isopropenylcyclopentene, cyclopentadiene, methylcyclopentadiene, dimethylcyclopentadiene, trimethylcyclopentadiene, methoxycyclopentadiene, methylmethoxycyclopentadiene, cyclohexylcyclopentadiene, isopropylcyclopentadiene, isopropenylcyclopentadiene, cyclohexene, methylcyclohexene, dimethylcyclohexene, trimethylcyclohexene, methoxycyclohexene, methoxymethylcyclohexene, cyclohexylcyclohexene, isopropylcyclohexene, isopropenylcyclohexene, cyclohexadiene, methylcyclohexadiene, dimethylcyclohexadiene, trimethylcyclohexadiene, methoxycyclohexadiene, methoxymethylcyclohexadiene, cyclohexylcyclohexadiene, isopropylcyclohexadiene, isopropenylcyclohexadiene, cycloheptene, methylcycloheptene, dimethylcycloheptene, trimethylcycloheptene, methoxycycloheptene, methoxymethylcycloheptene, cyclohexylcycloheptene, isopropylcycloheptene, isopropenylcycloheptene, cycloheptadiene, methylcycloheptadiene, dimethylcycloheptadiene, trimethylcycloheptadiene, methoxycycloheptadiene, methoxymethylcycloheptadiene, cyclohexylcycloheptadiene, isopropylcycloheptadiene, isopropenylcycloheptadiene, cycloheptatriene, methylcycloheptatriene, dimethylcycloheptatriene, trimethylcycloheptatriene, methoxycycloheptatriene, methoxymethylcycloheptatriene, cyclohexylcycloheptatriene, isopropylcycloheptatriene, isopropenylcycloheptatriene, cyclooctene, methylcyclooctene, dimethylcyclooctene, trimethylcyclooctene, methoxycyclooctene, methoxymethylcyclooctene, cyclohexylcyclooctene, isopropylcyclooctene, isopropenylcyclooctene, cyclooctadiene, methylcyclooctadiene, dimethylcyclooctadiene, trimethylcyclooctadiene, methoxycyclooctadiene, methoxymethylcyclooctadiene, cyclohexylcyclooctadiene, isopropylcyclooctadiene, isopropenylcyclooctadiene, cyclooctatriene, methylcyclooctatriene, dimethylcyclooctatriene, trimethylcyclooctatriene, methoxycyclooctatriene, methoxymethylcyclooctatriene, cyclohexylcyclooctatriene, isopropylcyclooctatriene, isopropenylcyclooctatriene, cyclooctatetraene, methylcyclooctatetraene, dimethylcyclooctatetraene, trimethylcyclooctatetraene, methoxycyclooctatetraene, methoxymethylcyclooctatetraene, cyclohexylcyclooctatetraene, isopropylcyclooctatetraene, isopropenylcyclooctatetraene, 3-phenyl-1-cyclohexene, 3-(2-methoxyphenyl)-1-cyclohexene, 3-cyclohexenyltrimethylsilane, 3-cyclohexenyltrimethoxysilane, [243-cyclohexenyl)ethyl]trimethoxysilane, [2-(3-cyclohexenyl )ethyl-]triethoxysilane, tert-butylcyclohexene, p-menth-1-ene, phellandrene, and terpinolene.

Another preferred class of suitable cyclic alkenes is bicyclic alkenes of the general formula CnH2n–{2x+2}–yRy where n is the number of carbons in the primary bicyclic structure, x is the number of unsaturated sites in the primary bicyclic structure, and y is the number of non hydrogen substituents, R, on the primary bicyclic structure. In this class of cyclic alkenes, n is an integer from 5 to 18, x is an integer and $x \leq n/2$, y is an integer and $0 \leq y \leq 2n-(2x+2)$, and each R can independently be $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent. A more preferred range of values for n is 6 to 14, and a most preferred range is 7 to 12. Examples of this class include, but are not limited to, 3-carene, alpha-pinene, norbornene, norbornadiene, bicyclo[2.2.2]octa-2,5, 7-triene, Rbicycloheptenyl)ethylltrimethoxysilane, hexamethyldewarbenzene, bicyclo[4.3.0]nona-3,7-diene, 1,4,5,8-tetrahydronaphthalene, 2,3-dimethyl-1,4,5,8-tetrahydronaphthalene, bicyclo[4.3.0]nona-3,7-diene, bicyclo[4. 1.1 ]oct-3-ene, bicyclo[4.2.0]oct-3-ene, bicyclo

[4.2.0]octa-2,4-diene, 5-(bicyclo[2.2.1]hept-2-enyl)triethoxysilane, bicyclo[4.2.0]octa-2,7-diene, bicyclo[4.3.0]nona-3,6-diene,5-vinyl-2-norbornene and 5-ethylidene-2-norbornene.

Another preferred class of cyclic alkenes is tricyclic alkenes of the general formula CnFl2n−qx+4)−Ry where n is the number of carbons in the primary tricyclic structure, x is the number of unsaturated sites in the primary tricyclic structure, and y is the number of non hydrogen substituents, R, on the primary tricyclic structure. In this class, n is an integer from 7 to 18, x is an integer and x 5 n/2, y is an integer and 0 5 y 5 2n−(2x+4), each R can independently be $C_1$-$C_{18}$ linear, branched, unsaturated or cyclic alkyl, $C_1$-$C_{18}$ linear, branched, unsaturated or cyclic alkoxy, substituted or unsubstituted aryl, or substituted silicon containing substituent. A more preferred range of values for n is 8 to 14, and a most preferred range is 9 to 12. Examples include, but are not limited to, dicyclopentadiene, 1,2,3,4,4A,5,8,8Aoctahydro-1,4-methanonapthalene, octamethyltricyclo[4.2.0.0(2,5)]octa-3,7-diene, 1,4-dihydro-1,4-methanonapthalene and [4.2.2]propella-2,4,7,9-tetraene.

Examples of R in each of the three classes of preferred cyclic alkenes described above include, but are not limited to, methyl, ethyl, propyl, isopropyl, isopropenyl, butyl, phenyl, methylphenyl, trimethylsilyl, cyclohexyl, methoxy, ethoxy, propoxy, isopropoxy, isopropenoxy, butoxy, phenoxy, methylphenoxy, trimethylsiloxy, or cyclohexloxy. Preferred examples of R include methyl, isopropyl, and isopropenyl. Methyl, isopropyl and isopropenyl are most preferred for R for use in semiconductor applications.

Preferred cyclic alkenes include dipentene, phellandrene, dicyclopentadiene, alpha-terpinene, gamma-terpinene, limonene, alphapinene, 3-carene, terpinolene, norbornene, norbornadiene, 5-vinyl-2-norbornene, and 5-ethylidene-2-norbornene. The most preferred cyclic alkenes are dicyclopentadiene, alpha-terpinene, norbornene, norbornadiene, 5-vinyl-2-norbornene, and 5-ethylidene-2-norbornene.

Suitable phenolic stabilizers of the disclosure are described by Formula (I) with the proviso that the boiling point is lower than 265° C. $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl. Examples of suitable $R^1$ through $R^5$ include, but are not limited to, H, OH, methyl, ethyl, propyl, isopropyl, butyl, isobutyl, tert-butyl, cyclohexyl, methoxy, ethoxy, propoxy, isopropoxy, butoxy, tert-butoxy, cyclohexloxy, phenyl or methylphenyl. Preferred examples of $R^1$ through $R^5$ in Formula (I) include H, OH, methyl, ethyl, methoxy, ethoxy, and tert-butyl. Most preferred examples are H and methoxy.

Suitable examples of Formula (I) include, but are not limited to, phenol, 4-methylphenol, 3-methylphenol, 2-methylphenol, 4-ethylphenol, 4-propylphenol, 4-iso-propyiphenol, 4-butylphenol, 4-sec-butylphenol, 4-isobutylphenol, 4-tert-butylphenol, 4-methoxyphenol(HQMME), 3-methoxyphenol, 2-methoxyphenol, 4-ethoxyphenol, 2-(1-methylbutyl)phenol, 2-tert-butyl-6-methylphenol, and 1,2-dihydroxybenzene. Preferred stabilizers of Formula (I) include phenol, 4-methylphenol, 3-methylphenol, 2-methylphenol, 4-methoxyphenol, 3-methoxyphenol, and 2-methoxyphenol. The most preferred stabilizer of Formula (I) is 4-methoxyphenol.

A suitable concentration of phenolic additive may be obtained from a range of concentrations greater than 200 ppm. Suitable concentration ranges are dependent on the specific stabilizer that is used and the injector and delivery conditions—For example, suitable ranges are greater than 200 ppm to 20000 ppm, preferably from 500 ppm to 10000 ppm, more preferably from about 1000 ppm to 5000 ppm, most preferably from about 3000 ppm to about 5000 ppm, The stabilizer and concentration necessary for extension of shelf life (static stability) may not be sufficient for successful delivery through a heated vapor injector (dynamic stability). In addition, the stabilizer and concentration necessary for successful delivery through a heated vapor injector (dynamic stability) may depend on the temperature of the injector.

The stabilized cyclic alkene composition may include a single phenolic additive or a mixture of two or more phenolic additives. The mixture of two or more phenolic additives may be present in any relative proportion to each other.

The stabilized cyclic alkene may be used in combination with a compound selected from a second stabilizer class, such as but not limited to benzophenones, substituted benzophenones, nitroxyl radicals, and substituted nitroxyl radicals.

The cyclic alkenes can be obtained commercially or by synthetic techniques known to those in the art. In commercial materials chemical manufacturers who make cyclic alkenes, will often stabilize their products with relatively high concentrations of BHT. Since most manufacturers are not accustomed to making high purity products, their product handling techniques can be relatively poor, and air, moisture and other contaminants can possibly enter the container before, during or after filling. These contaminants, once closed off into the container, can cause considerable degradation to the product if it is stored for any length of time. For semiconductor purposes, the commercial materials must be purified to remove all byproducts, and additives. This can be achieved by known purification or separation methods which may include but is not limited to techniques such as distillation, adsorption, sublimation, filtration and centrifugation.

However, to maintain purity and stabilization during purification, storage, and shipping, the cyclic alkene and compositions of the disclosure must be handled under strictly controlled conditions. These may include: addition of stabilizer to the product receiver prior to distillation so that product is immediately stabilized once it enters the product receiver, performing distillations under dry, inert atmospheres, rigorously cleaning and drying containers before use, using closed-filling techniques that prevent the product from being exposed to air, filling in a cleanroom to avoid dust and trace metal contamination that could act as polymerization catalysts, judicious choice of containers to prevent exposure to air or other incompatible materials and the implementation of final purge step with an inert gas containing very low levels of oxygen and water to minimize the oxygen and water content of the as-packaged chemical.

Many chemical precursors and precursor compositions for the semiconductor industry are typically packaged, shipped and stored in stainless steel containers to retain product quality for the maximum amount of time. The product container is then connected to chemical delivery equipment that transfers the chemical by a precisely controlled means, to retain product and process purity and consistency, to process equipment, referred to here as a film deposition tool.

The compositions of the disclosure may be used in any suitable chemical vapor deposition process which requires a cyclic alkene. Preferred processes are those chemical vapor deposition processes employing a silicon containing compound to deposit a low dielectric constant film. Examples of suitable processes include, but are not limited to those described in U.S. Pat. Nos. 6,815,373, 6,596,627, 6,756,323, 6,541,398, 6,479,110, 6,846,515, and 6,583,048 herein incorporated by reference.

The present disclosure is also directed to a process of using a cyclic alkene composition for forming a layer of carbon-doped silicon oxide on a wafer. The process comprises the steps of:
  a) providing a cyclic alkene composition in a container, a silicon containing compound in a container, a film deposition tool, a film deposition chamber within said film deposition tool, a means for connecting the containers to the film deposition chamber within said film deposition tool, a stream of carrier gas to sweep the cyclic alkene composition and the silicon containing compound through the connecting means into the film deposition chamber, and a substrate within the film deposition chamber of the film deposition tool;

b) introducing the vapors of the cyclic alkene composition and the silicon containing compound into the carrier gas stream;

c) transporting the vapor of the cyclic alkene composition and silicon containing compound into the film deposition chamber; and d) using one or more energy means, to form a carbon doped silicon oxide film on the substrate, wherein said cyclic alkene composition comprises:

1) one or more substituted or unsubstituted cyclic alkenes, and 2) an stabilizer composition comprising at least one compound of Formula (I), wherein the stabilizer composition is present in a concentration greater than 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl with the proviso that the components of the stabilizer composition have boiling point(s) lower than 265° C.

3) The cyclic alkenes suitable for this disclosure are the same as described previously.

Silicon containing compounds suitable for this disclosure include any class of silicon containing molecule such as silanes, alkylsilanes, alkoxysilanes, alkylalkoxysilanes, carboxysilanes, alkylcarboxysilanes, alkoxycarboxysilanes, alkylalkoxycarboxysilanes, linear siloxanes, cyclic siloxanes, fluorinated silanes, fluorinated alkylsilanes, fluorinated alkoxysilanes, fluorinated alkylalkoxysilanes, fluorinated carboxysilanes, fluorinated alkylcarboxysilanes, fluorinated alkoxycarboxysilanes, fluorinated alkylalkoxycarboxysilanes, fluorinated linear siloxanes, fluorinated cyclic siloxanes, and mixtures thereof.

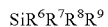 

$$SiR^6R^7R^8R^9 \qquad \text{Formula II:}$$

Suitable examples of silicon containing compounds of the disclosure are those described by Formula (II). In Formula (II), $R^6$ through $R^9$ can each independently be H, F, OH, $C_1$-$C_8$ linear, branched or unsaturated alkyl, $C_1$-$C_8$ linear, branched or unsaturated, alkoxy, substituted or unsubstituted cyclic or cyclic alkoxy, substituted or unsubstituted aryl or aryl alkoxy, substituted silicon containing substituent, partially or fully fluorinated $C_1$-$C_8$ linear, branched or unsaturated alkyl, partially or fully fluorinated $C_l$-Ca linear, branched, unsaturated alkoxy, partially or fully fluorinated substituted or unsubstituted cyclic or cyclic alkoxy, partially or fully fluorinated substituted or unsubstituted aryl or aryl alkoxy, partially or fully fluorinated substituted silicon containing substituent, non-, partially or fully fluorinated carboxylate ligands, or mixtures thereof. Examples of $R^6$ through $R^9$ in Formula (II) include, but are not limited to, H, F, OH, methyl, ethyl, propyl, isopropyl, isopropenyl, butyl, phenyl, methylphenyl, cyclohexyl, methyicyclohexyl, methoxy, ethoxy, propoxy, isopropoxy, butoxy, phenoxy, methylphenoxy, cyclohexyloxy, methylcyclohexyloxy, trifluoromethyl, trifluoroethyl, penatafluoroethyl, trifluoropropyl, pentafluoropropyl, heptafluoropropyl, isopropyl, hexafluoroisopropyl, trifluoroisopropenyl, trifluorobutyl, pentafluorobutyl, nonafluorobutyl, trifluorophenyl, (trifluoromethyl)tetrafluorophenyl, undecafluorocyclohexyl, (trifluoromethyl)decafluorocyclohexyl, trifluoromethoxy, trifluoroethoxy, pentafluoroethoxy, trifluoropropoxy, pentafluoropropoxy, heptafluoropropoxy, hexafluoroisopropoxy, heptafluoroisopropoxy, trifluorobutoxy, pentafluorobutoxy, nonafluorobutoxy, pentafluorophenoxy, (trifluoromethyl)tetrafluorophenoxy, undecafluorocyclohexyloxy, (trifluoromethyl)decafluorocyclohexyloxy, dimethylsiloxy (in the case of linear siloxanes), trimethylsiloxy, trimethyldisiloxy, pentamethyldisiloxy, diethylsiloxy, triethylsiloxy, triethyldisiloxy, pentaethyldisiloxy, dimethoxysiloxy, trimethoxysiloxy, trimethoxydisiloxy, pentamethoxydisiloxy, diethoxysiloxy, triethoxysiloxy, triethoxydisiloxy, pentaethoxydisiloxy, r1²-trimethyltrisiloxy (in the case of cyclic siloxanes, such as tetramethylcyclotetrasiloxane) and 71²-hexamethyltrisiloxy (in the case of cyclic siloxanes, such as octamethylcyclotetrasiloxane). Preferred examples of $R^6$ through $R^9$ include H, F, methyl, methoxy, ethyl, ethoxy and siloxy. For Formula (II), H, methyl, ethoxy and substituted siloxy are most preferred for $R^6$ through $R^9$ for use in semiconductor applications.

Examples of silicon containing compounds suitable for this disclosure include, but are not limited to, silane, methylsilane, dimethylsilane, trimethylsilane, tetramethylsilane, ethylsilane, diethylsilane, triethylsilane, tetraethylsilane, propylsilane, dipropylsilane, tripropylsilane, tetrapropylsilane, isopropylsilane, diisopropylsilane, triisopropylsilane, tetraisopropylsilane, butylsilane, dibutylsilane, tributylsilane, tetrabutylsilane, methyltrimethoxysilane, dimethyldimethoxysilane, trimethylmethoxysilane, trimethoxysilane, tetramethoxysilane, methylmethoxysilane, methyldimethoxysilane, methyltriethoxysilane, dimethyldiethoxysilane, trimethylmethoxysilane, tetraethoxysilane, methylethoxysilane, methyldiethoxysilane, methylpropoxysilane, dimethyldipropoxysilane, trimethylpropoxysilane, tetrapropoxysilane, methyltriisopropoxysilane, dimethyldiisopropoxysilane, trimethylisopropoxysilane, tetraisopropoxysilane, methyldiisopropoxysilane, methylphenylsilane, methyldiphenylsilane, methyltriphenyjsilane, dimethyldiphenylsilane, trimethylphenylsilane, methyl (methylphenyl)silane, methyldi(methylphenyl)silane, methyltri(methylphenyl)silane, methylphenoxysilane, methyldiphenoxysilane, dimethyldiphenoxysilane, methyl(methylphenoxy)silane, methyldi(methylphenoxy)silane, dimethyldi(methylphenoxy)silane, methyl(cyclohexyl)silane, methyldi(cyclohexyl)silane, methyltri(cyclohexyl)silane, dimethyldi(cyclohexyl)silane, trimethyl(cyclohexyl)silane, methyl(methylcyclohexyl)silane, methyldi(methylcyclohexyl)silane, methyltri(methylcyclohexyl)silane, dimethyldi(methylcyclohexyl)silane, trimethyl(methylcyclohexyl)silane, methyl(cyclohexyloxy)silane, methyldi(cyclohexyloxy)silane, methyl(tricyclohexyloxy)silane, dimethyldi(cyclohexyloxy)silane, methyl(methylcyclohexyloxy)silane, methyldi(methylcyclohexyloxy)silane, methyltri(methylcyclohexyloxy)silane, dimethyldi(methylcyclohexyloxy)silane, silicon tetrafluoride, fluorotrimethylsilane, methyltris(trifluoromethoxy)silane, trifluoromethyltris(trifluoromethoxy)silane, fluorotriethoxysilane, triacetoxysilane, methoxytriacetoxysilane, vinyltriacetoxysilane, vinylmethyldiacetoxysilane, trimethylsilyl(trimethylsilyl)propynoate, trimethylsilyl (trimethylsiloxy)acetate, trimethylsilyltrifluoroacetate, tris(trifluoromethylsilyl)trifluoroacetate, triethylacetoxysilane, tri(trifluoroacetoxy)silane, methyltri(trifluoroacetoxy)silane, methoxytri(trifluoroacetoxy)silane, tetra (trifluoroacetoxy)silane, tetraacetoxysilane, phenyltriacetoxysilane, phenyldimethylacetoxysilane, phenyldimethoxyacetoxysilane, phenylacetoxytrimethylsilane, 1,1,1,3,3-pentamethyl-3-acetoxydisiloxane, methyltriacetoxysilaneethyltriacetoxysilane, methyltriacetoxysilane, methacryloxytrimethylsilane, ethyltriacetoxysilane, dimethyldiacetoxysilane, di-t-butoxydiacetoxysilane, dibenzyloxydiacetoxysilane, bis(trimethylsilyl)malonate, bis(trimethylsilyl)acetylenedicarboxylate, acryloxytrimethylsilane, acetoxytrimethylsilane, acetoxymethyldimethylacetoxysilane, triethyl(trifluoroacetoxy)silane, phenyltri(trifluoroacetoxy)silane, phenyldi(trifluoromethyl)acetoxysilane, (pentafluorophenyl)dimethylacetoxysilane, phenyldimethyl(trifluoroacetoxy)silane, phenyl(trifluoroacetoxy)trimethylsilane, (trifluorophenyl)acetoxytrimethylsilane, phenylacetoxytri(trifluoromethyl)silane 1,1,1,3, 3-penta(trifluoromethyl)-3-acetoxydisiloxane, (trifluoromethyl)triacetoxysilaneethyltriacetoxysilane, (trifluoromethyl)triacetoxysilane, (trifluoromethyl)(trifluoromethoxy)diacetoxysilane, methacryloxytri(trifluoromethyl)silane, (trifluoroethyl)triacetoxysilane, di(trifluoromethyl)diacetoxysilane, di-(nonafluoro-t-butoxy)diacetoxysilane, dibenzyloxydi(trifluoroacetoxy)silane, acryloxytri(trifluoromethyl)silane, acetoxytri(trifluoromethyl)silane, acetoxy(trifluoromethyl)dimethylacetoxysilane, (trifluoromethyl)silane, di(trifluoromethyl)silane, tri(trifluoromethyl)silane, tetra(trifluoromethyl)silane, (trifluoroethyl)sitane, di(trifluoroethyl)silane, tri(trifluoroethyl)silane, tetra(trifluoroethyl)silane, (trifluoropropyl)silane, di(trifluoropropyl)silane, tri(trifluoropropyl)silane, tetra(trifluoropropyl)silane, (hexafluoroisopropyl)silane, di(hexafluoroisopropyl)silane, tri(hexafluoroisopropyl)silane, tetra(hexafluoroisopropyl)silane, (trifluorobutyl)silane, di(trifluorobutyl)silane, tri(trifluorobutyl)silane, tetra(trifluorobutyl)silane, (trifluoromethyl)trimethoxysilane, di(trifluoromethyl)dimethoxysilane, tri(trifluoromethyl)methoxysilane, tetra(trifluoromethoxy)silane, (trifluoromethyl)methoxysilane, (trifluoromethyl)dimethoxysilane, (trifluoromethyl)triethoxysilane, di(trifluoromethyl)diethoxysilane, tri(trifluoromethyl)methoxysilane, tetra(trifluoroethoxy)silane, (trifluoromethyl)ethoxysilane, (trifluromethyl)diethoxysilane, (trifluoromethyl)propoxysilane, di(trifluoromethyDdipropoxysilane, tri(trifluoromethyl)propoxysilane, tetra(trifluropropoxy)silane, (trifluoromethyl)triisopropoxysilane, di(trifluoromethyl)diisopropoxysilane, tri(trifluoromethyl)isopropoxysilane, tetra(trifluoroisopropoxy)silane, (trifluoromethyl)diisopropoxysilane, (trifluoromethyl)phenylsilane, (trifluoromethyl)diphenylsilane, (trifluoromethyl)triphenylsilane, di(trifluoromethyl)diphenylsilane, tri(trifluoromethyl)phenylsilane, (trifluoromethyl)(methyl phenyl)silane, (trifluoromethyl)di(methylphenypsilane, (trifluoromethyl)tri(methylphenyl)silane, (trifluoromethyl)phenoxysilane, (trifluoromethyl)diphenoxysilane, di(trifluoromethyl)diphenoxysilane, (trifluoromethyl)(methylphenoxy)silane, (trifluoromethyl)di(methylphenoxy)silane, di(trifluoromethyl)di(methylphenoxy)silane, (trifluoromethyl)(cyclohexyl)silane, (trifluoromethyl)di(cyclohexyl)silane, (trifluoromethyl)tri(cyclohexyl)silane, di(trifluoromethyl)di(cyclohexyl)silane, tri(trifluoromethyl)(cyclohexyl)silane, (trifluoromethyl)(methylcyclohexyl)silane, (trifluoromethyl)di(methylcyclohexyl)silane, (trifluoromethyl)tri(methylcyclohexyl)silane, di(trifluoromethyl)di(methylcyclohexyl)silane, tri(trifluoromethyl)(methylcyclohexyl)silane, (trifluoromethyl)(cyclohexyloxy)silane, (trifluoromethyl)di(cyclohexyloxy)silane, (trifluoromethyl)tri(cyclohexyloxy)silane, di(trifluoromethyl)di(cyclohexyloxy)silane, (trifluoromethyl)(methylcyclohexyloxy)silane, (trifluoromethyl)di(methylcyclohexyloxy)silane, (trifluoromethyl)tri(methylcyclohexyloxy)silane, di(trifluoromethyl)di(methylcyclohexyloxy)silane, tri(trifluoromethoxy)silane, methyltri(trifluoromethoxy)silane, dimethyldi(trifluoromethoxy)silane, trimethyl(trifluoromethoxy)silane, methyl(trifluormethoxy)silane, methyldi(trifluoromethoxy)silane, methyltri(trifluoroethoxy)silane, dimethyldi(trifluoroethoxy)silane, trimethyl(trifluoromethoxy)silane, methyl(trifluoroethoxy)silane, methyldi(trifluoroethoxy)silane, methyl(trifluoropropoxy)silane, dimethyldi(trifluoropropoxy)silane, trimethyl(trifluoropropoxy)silane, methyltri(hexafluoroisopropoxy)silane, dimethyldi(hexafluoroisopropoxy)silane, trimethyl(hexafluoroisopropoxy)silane, methyldi(hexafluoroisopropoxy)silane, methyl(pentafluorophenyl)silane, methyldi(pentaphenyl)silane, methyltri(pentaphenyl)silane, dimethyl(pentafluorophenyl)silane, trimethyl(pentafluorophenyl)silane, methyl[(trifluoromethyl)phenyl]silane, methyldi[(trifluoromethyl)phenyl]silane, methyltriRtrifluoromethyl)phenyl]silane, methyl(pentafluorophenoxy)silane, methyldi(pentafluorophenoxy)silane, dimethyldi(pentafluorophenoxy)silane, methyl[(trifluoromethyl)phenoxy]silane, methyldi[(trifluoromethyl)phenoxyjsilane, dimethyldi[(trifluoromethyl)phenoxy]silane, methyl(undecafluorocyclohexyl)silane, methyldi(undecafluorocyclohexyl)silane, methyltri(undecafluorocyclohexyl)silane, dimethyldi(undecafluorocyclohexyl)silane, trimethyl(undecacyclohexyl)silane, methyl[(trifluoromethyl)cyclohexyl]silane, methyldi[(trifluoromethyl)cyclohexyl]silane, methyltri[(trifluoromethyl)cyclohexyl]silane, dimethyldiRtrifluoromethyl)cyclohexygsilane, trimethyl[(trifluoromethypcyclohexyl]silane, methyl(undecafluorocyclohexyloxy)silane, methyldi(undecafluorocyclohexyloxy)silane, methyltri(undecafluorocyclohexyloxy)silane, dimethyldi(undecafluorocyclohexyloxy)silane, methyl[(trifluoromethyl)cyclohexyloxy]silane, methyldi[(trifluoromethyl)cyclohexyloxy]silane, methyltriRtrifluoromethyl)cyclohexyloxylsilane, dimethyldifftrifluoromethyl)cyclohexyloxyjsilane, hexamethyldisiloxane, octamethyltrisiloxane, octa(trifluoromethyl)trisiloxane, trimethyltrisiloxane, diethyltrimethyltrisiloxane, trimethylcyclotrisiloxane, tetramethylcyclotetrasiloxane, pentamethylcyclopentasiloxane, tetraethylcyclotetrasiloxane, pentaethylcyclopentasiloxane, hexamethylcyclotrisiloxane, octamethylcyclotetrasiloxane, decamethylcyclopentasiloxane, vinylmethyldiethoxysilane vinylmethyldimethoxysilane, trimethylsilylacetylene, di(trimethylsilyl)acetylene, hexa(trifluoromethyl)disiloxane, octa(trifluoromethyl)trisiloxane, tris(trifluoromethyl)trisiloxane, tris(trifluoromethyl)cyclotrisiloxane, tetra(trifluoromethyl)cyclotetrasiloxane, octa(trifluoromethyl)cyclotetrasiloxane and mixtures thereof.

Preferred examples of silicon containing compounds in Formula (II) include trimethylcyclotrisiloxane, triethylcyclotrisiloxane, tetramethylcyclotetrasiloxane, tetraethylcyclotetrasiloxane, pentamethylcyclopentasiloxane, pentaethylcyclopentasiloxane, octamethylcyclotetrasiloxane, methyltriethoxysilane, vinylmethyldimethoxysilane, vinylmethyldiethoxysilane, trimethylsilylacetylene, bis(trimethylsilyl)acetylene, methyldimethoxysilane and methyldiethoxsilane. Tetramethylcyclotetrasiloxane, methyldiethoxysilane, dimethyldimethoxysilane and trimethylsilylacetylene are most preferred for use in the semiconductor industry.

In a typical chemical vapor deposition process requiring at least two precursors, there are several methods by which the components can be combined The precursors) can be transported from seperate containers through chemical delivery lines to a vaporizer means housed in the film deposition tool. The precursors can be transported from the container through the delivery line to the vaporizer means by a variety of techniques, including, but not limited to, pressurization of the container with an inert gas, use of a mechanical pumping mechanism, gravity feed, or combinations thereof.

Ideally, separate chemical delivery lines and vaporizer means are used for each precursor, however it is possible for two precursors to be vaporized using a single vaporizer means when the two precursors are chemically compatible It should be understood by those skilled in the art that the connection between the chemical vapor process line (5) and the deposition process chamber (4) can vary from deposition tool to deposition tool, depending on the requirements for the process. For example, designs may include various apparatuses that affect the mixing, heating, cooling, or distribution of gases within the system. These may include an apparatus having baffles to mix the gases, a heated zone to heat gases, a cooling zone to cool gases, a chamber to allow pressure equilibration, or a showerhead to distribute gases over the surface of a wafer. Due to the complexity of designs that are available in the market and their variability based on need driven by the process, the options are described only in general terms here.

In our general example, the precursor vapors are transported through the chemical vapor process line to the substrate in the deposition chamber by a stream of gas flowing past the vaporizer means. The stream of gas, having a flow rate of about 5 standard cubic centimeters per minute (sccm) to about 10,000 sccm, is often heated to enhance vaporization of the precursors to help keep the precursors in the vapor phase. The gas used may be inert, such as nitrogen, helium or argon, chosen simply to act as a means to transport the precursor vapor to the substrate, or it may be a reactive gas, such as oxygen, ozone, ammonia, nitrous oxide, carbon dioxide, carbon monoxide, $SiF_x$, silanes, silicon tetrafluoride, hydrazine and the like to enhance the deposition process.

A plasma may also be used to add energy to the precursor vapors and enhance the deposition. Additionally, the plasma may be pulsed on and off to change the properties of the deposited film. The plasma power and pulse duration are carefully selected to enhance the deposition of the precursors on the substrate, and to modify the chemical identity and properties of the layer deposited onto the substrate. The plasma may also be applied over a range of frequencies, where the high and low frequency plasma power may range from about 0 to several kilowatts. The substrate may also have a bias of between about 0 and about −400 VDC to enhance material transport to the substrate. The substrate may be heated from about 25° C. to about 500° C. to either cause thermal breakdown of the precursor on the substrate, or may be used to enhance the deposition of precursor on the substrate. Unreacted materials are exhausted through an exhaust line.

The elemental composition of the film, and thus the film properties, can be adjusted by the choice of starting silicon containing compound, the cyclic alkene employed, and the use or lack of use of various reactive gases in the process.

Subsequent to the film deposition, the initial film may be subjected to a curing step. The curing steps may also be employed to modify e.g. the density or elemental compositions of the films to change film properties such as film strength, dielectric constant and various other properties of the film. These curing steps may comprise a thermal treatment by the application of heat through one of various heating means such as hot plates, ovens, infrared lamps, or microwaves. Alternatively, the curing may comprise a plasma treatment, or a chemical treatment of the film. These curing steps may take place in an inert atmosphere (e.g. noble gases), a reducing atmosphere (e.g. hydrogen, or hydrocarbon), or an oxidizing atmosphere (e.g. oxygen, air, ozone, nitrous oxide, carbon dioxide) depending on the desired chemical change in the initial film. Such processes are described in the art and known to those skilled in the art.

Though the data above suggest that higher concentrations of stabilizer are preferred, the actual concentration needed is a fine balance between appropriate stabilization of the chemical (where higher concentrations are preferred) and reduction of the amount of potential residue, such as the stabilizer itself, that could be left behind (where lower concentrations are preferred).

The amount of stabilizer is greater than 200 to 20,000 parts per million (ppm), preferably 500 to 10,000 ppm, and more preferable 1000 to 5000 ppm, most preferably 3000 to 5000 ppm for dynamic stability at industry relevant direct liquid injection conditions.

EXAMPLES

Example 1

Residue Evaluation of Recently Distilled NBDE

A sample of NBDE was flash distilled to remove non-volatile impurities using a rotary-evaporator. The distilled material was analyzed by GC to have a nominal purity of 99.4%. The tare weight of an empty, clean 1.2 liter quartz bubbler was recorded after evacuation. The bubbler was previously equipped with gas inlet and outlet ports, each fitted with a Teflon valve. The bubbler inlet port had a dip-tube that extends to within ⅛" of the base of the container. About 600 g of NBDE was added to the quartz bubbler within a nitrogen-containing dry box. The bubbler was re-weighed to determine the weight of the NBDE. A cylinder of research grade He was connected to the bubbler inlet line. The bubbler temperature was increased to 35° C. to increase the vapor pressure of the NBDE. He was purged through the bubbler at a flow rate of 3.0 SLPM (standard liters per minute) for 4 hours to evaporate the NBDE. At this time the bubbler temperature was raised to 80° C. and the bubbler was evacuated for 2.0 hours to achieve a stable weight. This experiment was done in duplicate. The weights of the non-volatile residue for the two runs corresponds to an average residue of 0.05 wt. %. The experimental results are summarized in Table 1.

Example 2

Evaluation of the Degradation Rate of NBDE Stored at Ambient Temperature

A 13.0 liter sample of NBDE was purified by atmospheric distillation. The distilled sample was analyzed by GC to have a nominal purity of 99.4%. The sample was stored in a chemical cabinet indoors for a total of 287 days. At this time approximately 200 g of NBDE was loaded into a pre-cleaned, pre-tared bubbler as described in Example 1. The bubbler was subjected to 3.0 SLPM at 35° C. for 4.0 hours to evaporate the NBDE. The bubbler temperature was raised to 80° C. and the bubbler was evacuated for 2.0 hours to achieve a stable weight. The final weight of the bubbler was recorded after the evacuation step to determine the weight of the non-volatile residue. This experiment was done in duplicate. The weights of the non-volatile residue for the two runs corresponds to an average residue of 1.12 wt. %. The experimental results are summarized in Table 1.

Example 3

Evaluation of the Degradation Rate of Unstabilized NBDE Using Accelerated Aging Conditions A sample of NBDE was flash distilled to remove non-volatile impurities as described in Example 1. Approximately 150-200 g of the distilled NBDE was loaded into a cleaned, pre-tared bubbler as described in Example 1. The bubbler was placed into an oven and held at 80° C. for 7 days. The temperature of 80° C. was chosen for this study for two reasons: (1) 7 days at 80° C. is intended to simulate the amount of degradation that would occur if the sample were allowed to age at ambient temperature for 1 year, assuming that the degradation rate follows a simple Arrhenius type behavior of doubling for every temperature increase of 10° C.; and (2) 80° C. is a common temperature for the heated manifold used to vaporize precursors prior to the mixing bowl and/or deposition chamber in chemical vapor deposition hardware. The quartz bubbler was removed from the 80° C. oven after 7 days. The bubbler was held at 35° C. while purging with 3 SLPM of He for 6 hours. At this time the bubbler temperature was raised to 80° C. and the bubbler was evacuated for 2.0 hours to achieve a stable weight. The final weight of the bubbler was recorded after the evacuation step to determine the weight of the non-volatile residue. This experiment was run a total of 6 times, since it was used as the "control" for the evaluation of various stabilizers. The average non-volatile residue for these runs was 4.33 wt. %, The experimental results are summarized in Table 1.

Example 4

Figure 4:
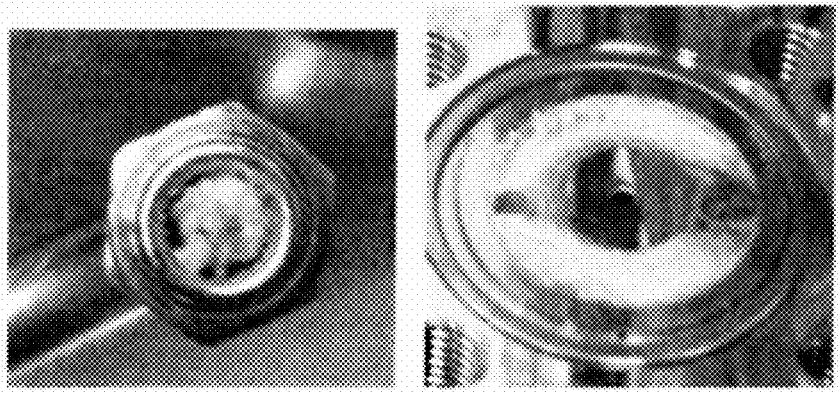
FIG. 4 are photographs of an injector port on the left and the injector face plate on the right after exposure to accelerated aged unstabilized NBDE during a dynamic flow test, showing considerable unacceptable solid residue.

Flow Test of Unstabilized, Accelerated Aged NBDE 100 grams of NBDE was freshly distilled. The liquid was then heated at 80 C for one week (accelerated aging) in order to simulate one year at room temperature. The expected non-volatile oligomer concentration was approximately 4 wt. percent, based on results from example 3, and the mechanism shown in FIG. 1. The liquid was transferred under inert atmosphere to an Air Products Chemguard liquid containment system. An applied materials Precision 5000 platform with Horiba STEC 2410 vapor injector was used to perform dynamic flow testing. The injector temperature was set to 70 C. Helium gas at a pressure of 30 psi was used to push the liquid to the vapor injector. An additional 200 sccm of helium was used as an inert carrier across the injector face. The downstream chamber pressure was set to 8 torr. The liquid flow was 1000 mg/min. After the flow test was complete, the injector was inspected for residue. A significant amount of solid material was found on the injector face and inside the exit port, as shown in FIG. 4. For comparison, a new injector face plate and port are shown in FIG. 3, where there is no residue present The residue build-up was determined to be >2 wt %. This is slightly less than the prediction from static testing, likely due to the loss of some powdery residue material in the vapor line and delivery system.

Example 5

Figure 5:
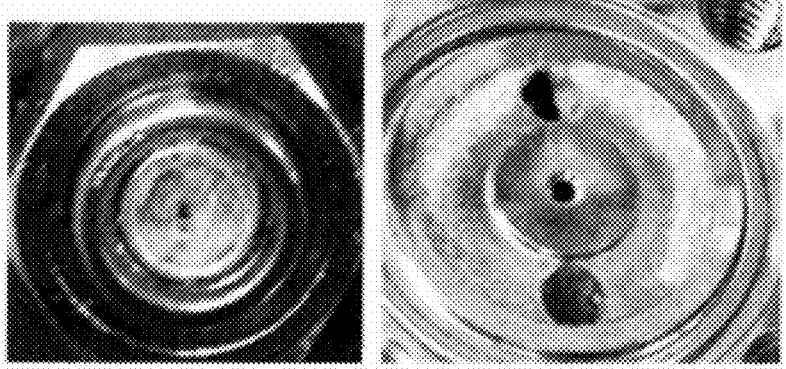
FIG. 5 are photographs of an injector port on the left and the injector face plate on the right after exposure to freshly distilled, unstabilized NBDE during a dynamic flow test, still showing unacceptable solid residue.

Flow Test of Unstabilized, Freshly Distilled NBDE 100 grams of NBDE was freshly distilled. The expected non-volatile oligomer concentration was zero. The liquid was transferred under inert atmosphere to an Air Products Chemguard liquid containment system. An applied materials Precision 5000 platform with Horiba STEC 2410 vapor injector was used to perform dynamic flow testing. The injector temperature was set to 80 C. Helium gas at a pressure of 30 psi was used to push the liquid to the vapor injector. An additional 400 sccm of helium was used as an inert carrier across the injector face. The downstream chamber pressure was set to 10 torr. The liquid flow was 1800 mg/min. Flow was cycled 3 minutes on, 2 minutes off, in order to simulate manufacturing conditions. Because there was no non-volatile residue present before vaporization, any residue that was formed was expected to occur in-situ at the injector, consistent with the mechanism shown in FIG. 2. After the flow test was complete, the injector was inspected for residue. A significant amount of solid material was found on the injector face and inside the exit port, as shown in FIG. 5. The weight was found to be >0.5% build-up. This is greater than the prediction of 0.05% from static testing, and indicates that there is additional residue formation due to a dynamic mechanism during delivery and use through the vaporizer system.

Example 6

Figure 6:
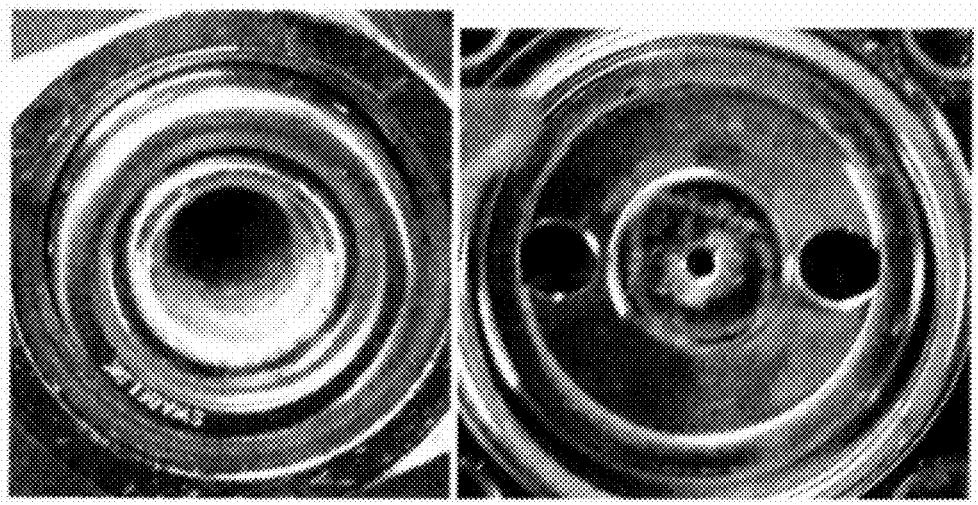
FIG. 6 are photographs of an injector port on the left and the injector face plate on the right after exposure to freshly distilled NBDE, stabilized with only 200 ppm of 4-methoxyphenol, during a dynamic flow test, still showing unacceptable solid residue. This is illustrative of the prior art.

Flow Test of NBDE Stabilized with 200 ppm of 4MP at 90 C Injector Temperature 100 grams of NBDE was freshly distilled and 200 ppm of 4MP was added. The expected non-volatile oligomer concentration after distillation was zero. The liquid was transferred under inert atmosphere to an Air Products Chemguard liquid containment system. An applied materials Precision 5000 platform with Horiba STEC 2410 vapor injector was used to perform dynamic flow testing. The injector temperature was set to 90 C. Helium gas at a pressure of 30 psi was used to push the liquid to the vapor injector. An additional 400 sccm of helium was used as an inert carrier across the injector face. The downstream chamber pressure was set to 10 torr. The liquid flow was 1800 mg/min. Flow was cycled 3 minutes on, 2 minutes off, in order to simulate manufacturing conditions. After the flow test was complete, the injector was inspected for residue. The injector was found to have a slight amount of residue on the face plate, and a coating of residue on the injector port, as shown in FIG. 6. Results are summarized in table 1. The residue weight was estimated to be >0.5 wt %. Therefore it is likely that 200 ppm is not a sufficient level to maintain dynamic stability.

Example 7

Figure 7:
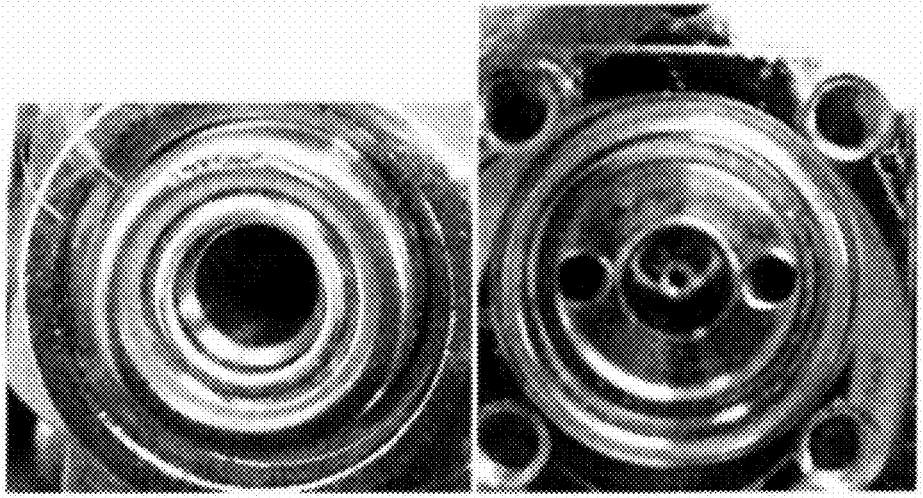
FIG. 7 are photographs of an injector port on the left and the injector face plate on the right after exposure to freshly distilled NBDE, stabilized with 1000 ppm of 4-methoxyphenol, during a dynamic flow test, surprisingly showing no solid residue. This is illustrative of the present invention's unexpected results in stabilizer concentration during the rigor of dynamic conditions of vaporization at an injector.

Flow Test of NBDE Stabilized with 1000 ppm of 4MP at 90 C Injector Temperature 100 grams of NBDE was freshly distilled and 1000 ppm of 4MP was added. The expected non-volatile oligomer concentration after distillation was zero. The liquid was transferred under inert atmosphere to an Air Products Chemguard liquid containment system. An applied materials Precision 5000 platform with Horiba STEC 2410 vapor injector was used to perform dynamic flow testing. The injector temperature was set to 90 C. Helium gas at a pressure of 30 psi was used to push the liquid to the vapor injector. An additional 400 sccm of helium was used as an inert carrier across the injector face. The downstream chamber pressure was set to 10 torr. The liquid flow was 1800 mg/min. Flow was cycled 3 minutes on, 2 minutes off, in order to simulate manufacturing conditions. After the flow test was complete, the injector was inspected for residue. The injector was found to be largely clean with an estimated build up of <0.1 wt %, as shown in FIG. 7. Results are summarized in table 1. Although there is not a clear differentiation between 200 and 1000 ppm of 4MP under static conditions, the impact can be seen using flow testing to simulate dynamic conditions.

TABLE 1

|  | Residue collect from static NVR testing after distillation (no aging) | Residue collected from static NVR testing after accelerated aging | Residue collected from dynamic flow testing after accelerated aging | Residue collected from dynamic flow testing after distillation (no aging) |
|---|---|---|---|---|
| NBDE unstabilized | 0.05% | >4 wt % | >2% wt | >0.5% wt |
| NBDE with 200 ppm 4MP | N/A | 0.2 wt % | N/A | Approx >0.5 wt % |
| NBDE with 1000 ppm 4MP | N/A | 0.1 wt % | N/A | Approx <0.1 wt % |

The invention claimed is:

1. A method of forming a layer of carbon-doped silicon oxide on a substrate, the method comprising the steps of:
providing a cyclic alkene composition in a first container, wherein the cyclic alkene is at least one compound selected from the group consisting of: dipentene, phellandrene, dicyclopentadiene, alpha-terpinene, gamma-terpinene, limonene, alphapinene, 3-carene, terpinolene, norbornene, norbornadiene, 5-vinyl-2-norbornene, and 5-ethylidene-2-norbornene, a silicon containing compound in a second container, a film deposition tool, a film deposition chamber within said film deposition tool, and a stream of carrier gas to sweep said cyclic alkene composition and said silicon containing compound through a connection into the film deposition chamber, wherein said substrate is disposed within said film deposition chamber of said film deposition tool;
connecting said first and second containers to said film deposition chamber within said film deposition tool;
introducing vapors of said cyclic alkene composition and said silicon containing compound into said carrier gas stream;
transporting said vapors of said cyclic alkene composition and said silicon containing compound into said film deposition chamber via the carrier gas stream; and
forming the layer of the carbon-doped silicon oxide on the substrate, wherein said cyclic alkene composition further comprises a stabilizer compound selected form the group consisting of: phenol, 4-methylphenol, 3-methylphenol, 2-methylphenol, 4-ethylphenol, 4-propylphenol, 4-iso-propylphenol, 4-butylphenol, 4-sec-butylphenol, 4-iso-butylphenol, 4-tertbutylphenol, 4-methoxyphenol, 3-methoxyphenol, 2-methoxyphenol, 4-ethoxyphenol, 2(1-methylbutyl)phenol, 2-tert-butyl-6-methylphenol, 1,2- dihydroxybenzene, 2,4-di-tert-butylphenol, 2,6-di-tert-butyl-4-methylphenol (BHT), 1,3-dihydroxybenzene, hydroquinone, 2-(benzyloxy)phenol, 3,4,5-trimethoxyphenol, 3-ethoxy-4-methylphenol, 4-benzyloxyphenol, 4-benzyl-2,6-di-tert-butylphenol, 2-(2-butenyl)phenol, 4-propoxyphenol, 4-butoxyphenol, 2-(4-methylbenzyl)phenol, 2,4,6-tris-benzyloxyphenol, 2,4-dicyclohexy1-5-methylphenol, 6-tert-butyl-1,2-dihydroxybenzene and mixtures thereof,
wherein the stabilizer composition is present in a concentration of from 500 ppm up to 10,000 ppm, and wherein said stabilizer compound has a boiling point lower than 265° C.

2. The method of claim 1, wherein said stabilizer compound is 4-methoxyphenol.

3. The method of claim 1 wherein the stabilizer is present in the range of from 1000 to 5000 ppm.

4. The method of claim 1 wherein the stabilizer is present in the range of from 3000 to 5000 ppm.

* * * * *

UNITED STATES PATENT AND TRADEMARK OFFICE
CERTIFICATE OF CORRECTION

| | | |
|---|---|---|
| PATENT NO. | : 8,173,213 B2 | |
| APPLICATION NO. | : 12/470002 | |
| DATED | : May 8, 2012 | |
| INVENTOR(S) | : Steven Gerard Mayorga et al. | |

It is certified that error appears in the above-identified patent and that said Letters Patent is hereby corrected as shown below:

In the Claims:

Column 19, Line 42

In Claim 1 delete "comprises" and insert -- comprises: --

Column 20, Line 16

In Claim 1 delete the word "form" and insert -- from --

Signed and Sealed this
Twenty-third Day of April, 2013

Teresa Stanek Rea
*Acting Director of the United States Patent and Trademark Office*